United States Patent [19]

Raines

[11] Patent Number: 4,615,694
[45] Date of Patent: Oct. 7, 1986

[54] VENTED CONE FILTER

[75] Inventor: Kenneth C. Raines, Bethlehem, Pa.

[73] Assignee: Burron Medical Inc., Bethlehem, Pa.

[21] Appl. No.: 702,357

[22] Filed: Feb. 15, 1985

[51] Int. Cl.$^4$ .............................................. A61M 5/16
[52] U.S. Cl. ..................... 604/126; 604/406
[58] Field of Search ............... 604/126, 256, 403, 405, 604/406

[56] References Cited

U.S. PATENT DOCUMENTS

| | | | |
|---|---|---|---|
| 3,803,810 | 4/1974 | Rosenberg | 604/406 |
| 3,954,623 | 5/1976 | Hammer et al. | 604/252 |
| 4,004,587 | 1/1977 | Jess | 604/126 |
| 4,031,891 | 6/1977 | Jess | 604/126 |
| 4,198,971 | 4/1980 | Noiles | 604/126 |
| 4,294,594 | 10/1981 | Sloane, Jr. et al. | 604/126 |
| 4,298,358 | 11/1981 | Ruschke | 604/126 |

FOREIGN PATENT DOCUMENTS

WO81/02981 10/1981 PCT Int'l Appl. ................. 604/252

Primary Examiner—C. Fred Rosenbaum
Assistant Examiner—Michelle N. Lester
Attorney, Agent, or Firm—Shoemaker and Mattare, Ltd.

[57] ABSTRACT

A vented cone filter for use with intravenous liquids which may contain undesired particles as well as gas such as air therewith. A vented chamber of elongated tubular construction and provided with a pointed input opening at one end thereof receives a complementary mating end cap having an output opening therewith. Mounted within the chamber of the main body and supported by the end cap is a cone filter of plastic framework supporting a hydrophilic filter element therewith. Around the ouside of the chamber body appropriate openings are provided and a hydrophobic membrane encompasses same for allowing blocked gas within the chamber to be vented to the outside. Preferably, a sleeve is molded over the hydrophobic membrane once installed for securement and protection thereof.

As well as the structure of the present invention, the method of making of same is also encompassed by this invention.

8 Claims, 5 Drawing Figures

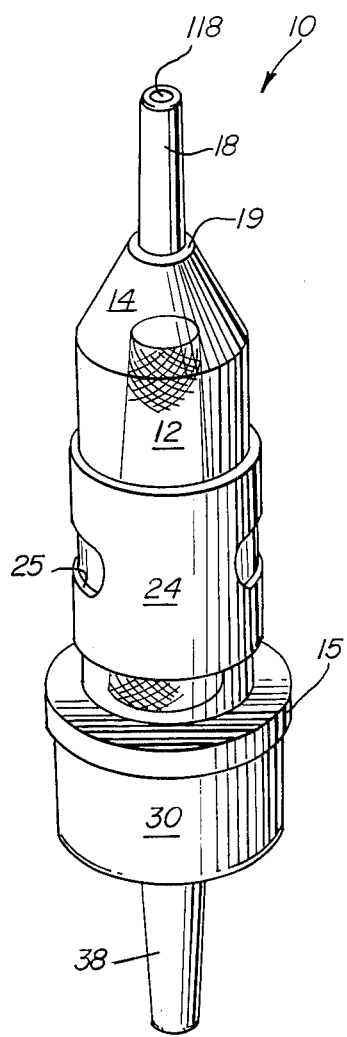
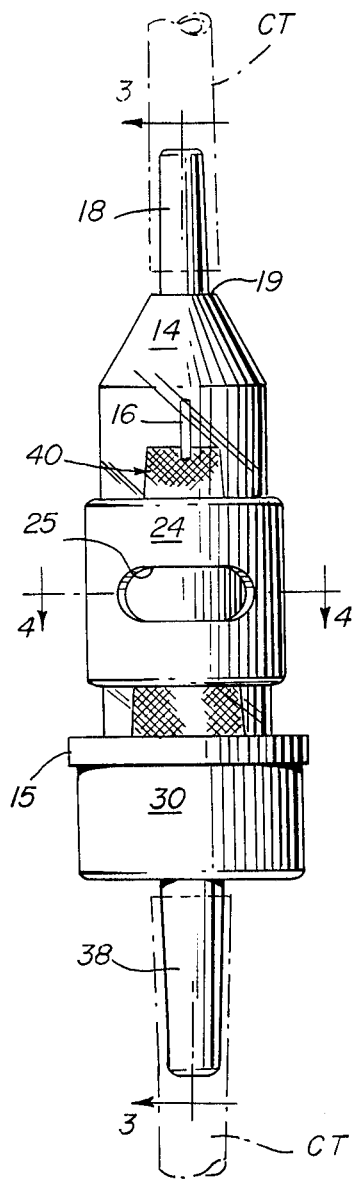
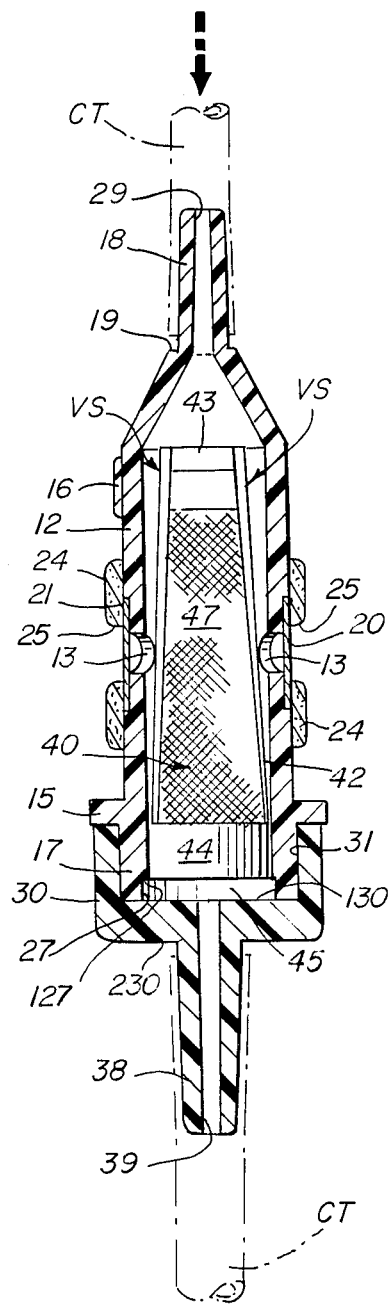
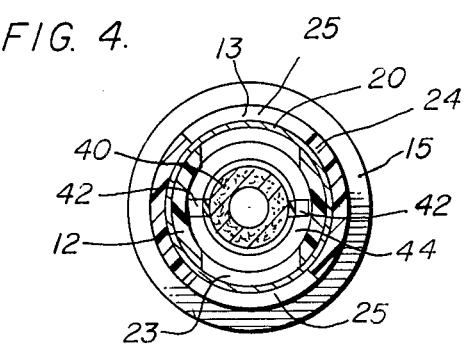

VENTED CONE FILTER

BACKGROUND OF THE INVENTION

1. Field of the Invention

This invention relates generally to devices for use in administration of intravenous solutions, and especially for filters for use in such systems.

2. Description of the Prior Art

When administering intravenous solutions, it is generally desirable to filter such solutions just prior to their infusion into a patient in order to remove solid particulate matter such as bacteria, undesirable solids, and any particulates greater than a few microns. Known type filters for effecting this filtering are generally employed, such as hydrophilic filters. Such filters, after being wetted, are capable of passing liquid through the pores thereof while simultaneously blocking air or like gases. Thus, such filters can substantially remove any of the particulates which are considered to be undesirable.

Also, it is extremely important that any air or other gases which might be present in the solution be blocked and preferably eliminated from the system prior to the administration of the solution into a patient.

However, known type devices for effecting the above functions oftentimes leave much to be desired. A common problem with such devices is that they may filter out the particulate materials, but gas blockage of the filter can result with subsequent blocking of the entire filter and prevention of the fusion flow therethrough.

Another common problem with known type devices is that even though gases such as air may be blocked by the filter, they fail to completely expel or eliminate such air. This, of course, is very important so that there is no possibility of the gases either becoming re-entrained with the solution and/or being infused into the patient with oftentimes fatal results.

Several known patents which are pertinent to the present invention are U.S. Pat. Nos. 4,004,587 and 4,031,891.

In U.S. Pat. No. 4,004,587, a filter device which is conical in nature is used with tubing for administration of parenteral fluids. The filter device is conical and provided with two window sections in the filter support housing, one of the window sections being covered with a hydrophilic filter, and the other window section with a hydrophobic filter, However, the first and second separate filter members are in parallel flow position so that simultaneous flow can occur therethrough in parallel relationship. This is quite different from the device of the present invention.

U.S. Pat. No. 4,031,891 shows a filter arrangement having a housing with both a hydrophobic and a hydrophilic filter element. However, the position of the elements in this device is substantially different and unlike that of the structure of the present invention. In this patent both the fluid and air are purged from inside the tube. In the present device, the one filter separates air from the fluid prior to the fluid itself passing through the hydrophilic membrane and subsequent infusion into a patient.

Furthermore, in U.S. Pat. No. 4,004,587, air is expelled from inside the cone, through the hydrophobic membrane and into the fluid path. This arrangement is fine for initial priming, but can be dangerous is air should enter the system when connected to a patient.

None of the known prior art devices offer the new and novel features of the present invention.

SUMMARY OF THE INVENTION

An object of the present invention is to provide a filter for use in the administration of intravenous solutions which overcomes the disadvantages set forth above.

Another object of the present invention is to provide a filter for use with intravenous fluids which is air blocking and air eliminating.

A further object of this invention is to provide an air blocking and eliminating filter which is capable of providing high fluid flow and yet which will positively eliminate any air in the fluid, as well as block particulates of very small size.

Another still further object of the present invention is to provide a filter having a cone type hydrophilic filter element capable of passing liquid therethrough but simultaneously blocking gases together with a hydrophobic filter capable of blocking liquid flow therethrough and yet passing gases therethrough. Thus, this filter will catch small particulates in the fluid flow, and yet block and eliminate any gases contained in such fluid.

A still further object of this invention is to provide a filter structure having a vented chamber with a hydrophobic membrane thereover together with hydrophilic cone type filter within such chamber for passing fluids therethrough and yet blocking both gases and particulates from passing therethrough.

The present invention has a number of new and novel features. Among them are the fact that small particulates down to 5 microns or so in size can be caught and blocked by a cone filter element contained within the vented chamber main body member. The vented chamber main body member also is provided with two oppositely opposed openings for egress of any gases such as air from the chamber. Of course, such air would be very undesirable for infusion into a patient, and in some cases, could even be fatal. Therefore, it is extremely important that any such air or other gases be completely eliminated from a fluid being administered. A hydrophobic membrane is provided over the spaced openings and retained in place by spot welding or gluing and covered with a sleeve over-mold for securement and retention thereof.

An end cap on the opposite end of the vented chamber input opening has a projection with outlet opening extending therefrom. This end cap is used to secure the cone filter element within the vented chamber main body member. Appropriate epoxy and/or ultrasonic welding of the cap to the vented chamber body element permanently fastens the two units together.

Of course, in use for administering intravenous liquids into a patient, the fluid is inputted into the input of the vented chamber whereupon the hydrophilic cone filter will allow the liquids to pass, yet will block any particles of small size, as well as blocking any gases such as air. Such gases will then be expelled through suitable apertures in the main body element. A thin membrane member of hydrophobic material allows escape of the gases, but blocks any fluid flow therethrough.

An end cap with the vented chamber securely holds the hydrophilic cone filter element in place in a permanent manner and a sleeve over-mold over the hydrophobic membrane securely fastens and retains same around the vented chamber main body element.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of the filter of the present invention.

FIG. 2 is a side elevational view of the filter of FIG. 1.

FIG. 3 is a cross-sectional view taken along line 3—3 of FIG. 2.

FIG. 4 is a top plan view taken along line 4—4 of FIG. 2.

DESCRIPTION OF THE PREFERRED EMBODIMENT

Figure 5:
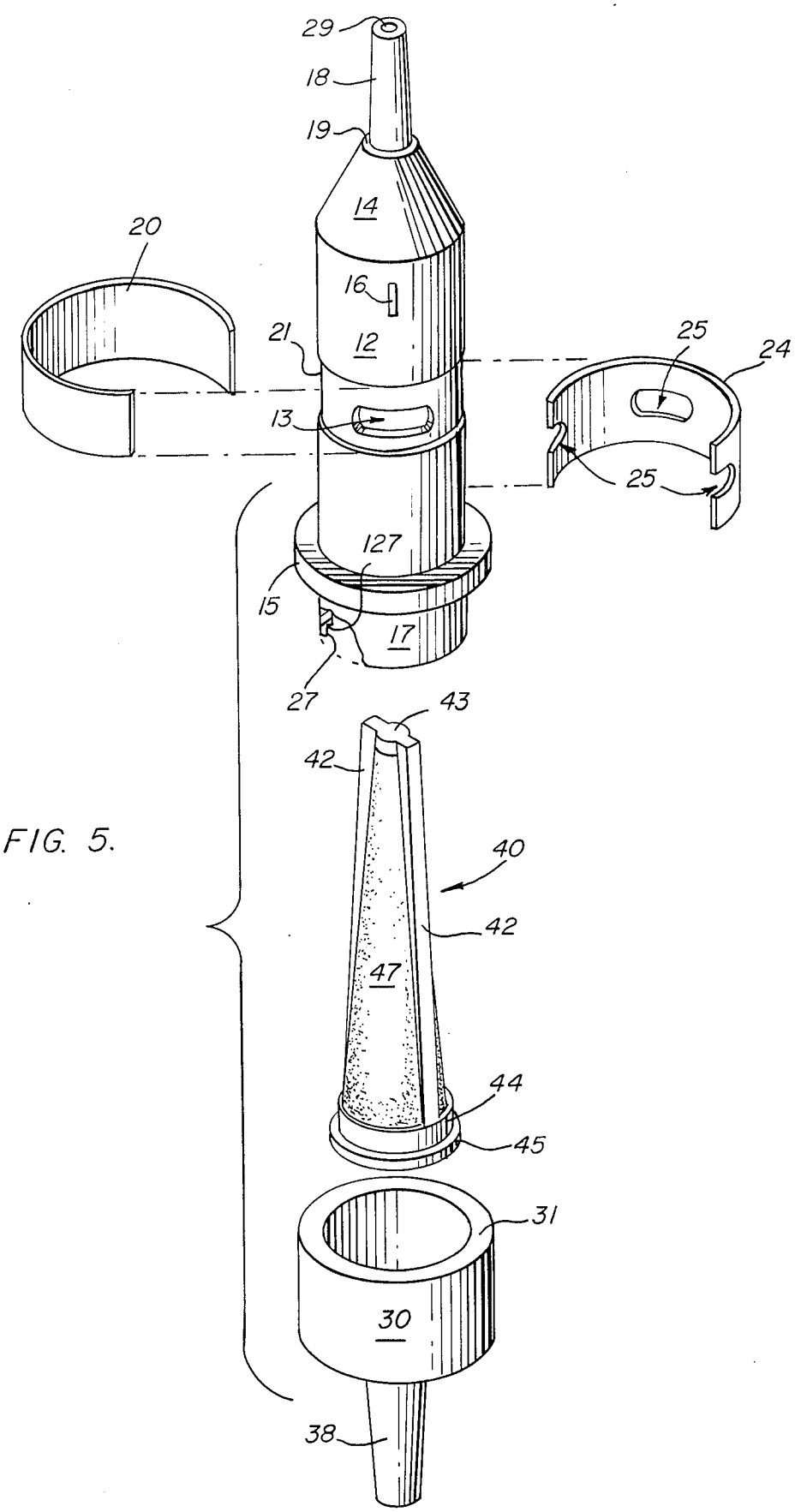
FIG. 5 is an exploded perspective view of the filter of the present invention showing the component elements thereof.

Referring to FIG. 1 of the drawing, reference numeral 10 indicates in general the filter of the present invention. This filter comprises a vented chamber main body element 12 having a conical nose portion 14 ending in a projecting tubing receiving attachment 18. An input channel 118 extends longitudinally of the projecting attachment 18 for inputting of intravenous fluids and the like therethrough. As shown in FIGS. 2 and 3, flexible coupling tubing CT is appropriately attached to the attachment projection 18. A small shoulder 19 between projection 18 and conical portion 14 provides an abutment surface for the coupling tubing CT. As best seen in FIGS. 2, 3, and 5, a key 16 is provided externally of the vented chamber body element 12 near the junction with the conical portion 14.

The other end of the body element 12 is provided with a radial flange portion 15 and an extension 17. The extension 17 has a small recess portion 27 therewithin which has a shoulder 127 for use in engagement with and ultrasonic sealing of the hydrophilic cone filter element 40 within the main body element. As best seen in FIGS. 3 and 5, the cone filter element 40 has a plastic support structure 42, 43, and 44. The two diametrically opposed, thin support elements 42 connect the cone end 43 with the cone base 44. The actual filter membrane 47 comprises a hydrophilic material which will allow liquid passage, but block any gases from flow therethrough. The base 44 of the cone filter has a small flange 45 extending therefrom which complements with the recessed area 27 in the end extension 17 of the vented chamber main body element. Thus, when the cone filter 40 is inserted into the main body element 12, the edge of the flange 45 will abut against the shoulder 127 (as shown in FIG. 3) to positively position the cone filter within the vented chamber 12. When so mounted a void space VS is provided between the cone filter and the interior of the chamber body member 12.

An end cap 30 is suitably affixed by ultrasonic welding, epoxy, or the like, to the extension 17. The inner surface 130 of this end cap 30 will abut against the bottom surface of the base 44 and flange 45 to securely affix the cone filter within the vented chamber. Affixed to the cap 30 is an outlet projection 38 having an output channel 39 therethrough. As best seen in FIGS. 2 and 3, appropriate coupling tubing CT also is connected to this outlet projection 38. The outer surface 230 of the end cap 30 will also limit the mounting of coupling tubing CT upon outlet projection 38.

The vented chamber main body element 12 is provided with a pair of gas egress openings 13 which in turn are covered by a hydrophobic membrane 20. This membrane during installation is long enough to lap more than one turn around the chamber 12. The overlap portions are then glued or spot welded to affix same together. Thereafter, prior to completion of the overall filter, a sleeve member 24 is applied over the edges of the membrane and the recessed portion 21 within the vented chamber. This sleeve 24 has appropriate apertures 25 therewithin to line up with the openings 13 of the vented chamber 12. Preferably, the sleeve 24 is over-molded, that is, applied by additional molding procedure over the overall filter device as completed so far.

The method of making the filter of the present invention is also part of this invention. Initially, the main vented chamber body element is molded with the end 17, flange 15, main cylindrical portion 12, conical end 14 and end attachment projection 18. The holes 13 can preferably be formed during the same molding process, or, in some cases, could be cut into the material or punched thereinto later. The end cap structure 30 is similarly suitably molded in a plastic mold to have the configuration shown. A cone filter 40 having a hydrophilic membrane 47 therewith is then molded and made. This cone filter is then installed within the vented chamber main body element 12 and the end cap is attached and secured by ultrasonic welding or the like. Thereafter, a hydrophobic membrane 20 is wrapped around the vented chamber main body element over the apertures 13 therein and the overlapped ends of the membrane secured. Thereafter, further over-molding is used to apply and hermetically seal the retaining sleeve 24 over the edges of the membrane and with appropriate gas egress openings 25 aligned with the openings 13 in the main body element. The device now is ready for sterile packaging and distribution.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. The method of making a filter for use in filtering intravenous liquids and removing air therefrom including the following steps:
   providing a hollow, elongated tubular member;
   providing side openings in said tubular member;
   covering said side openings with a membrane of hydrophobic material;
   overmolding the hydrophobic material with a plastic sleeve to provide a hermetic seal;
   inserting a cone-shaped filter element of hydrophilic material into the inner hollow of the tubular element;
   enclosing a free end of said chamber with an end cap having a liquid output opening therein; and
   ultrasonically sealing the hydrophilic filter, tubular member, and end cap in one operation.

2. The method of making a filter as defined in claim 1, wherein said hydrophobic membrane has overlapped ends secured in position prior to the plastic sleeve being placed therearound.

3. A filter for eliminating air during administration of intravenous liquids comprising:

an elongated, hollow tubular body having a small fluid inlet opening at one end thereof, an output vent in the side thereof, and being closed at the other end by a suitable end cap fixed thereto;

said end cap having a fluid output projection with central opening extending therefrom;

a hydrophilic filter element supported within said body by said end cap, said hydrophilic element capable of passing aqueous liquid therethrough when wet while simultaneously blocking small particles as well as air flow therethrough; and a hydrophobic filter over said output vent in the side of the tubular body for repelling aqueous liquid and yet passing air therethrough so that any air in the inputting liquid will be locked by said hydrophilic filter and expelled out of the overall device by said hydrophobic filter.

4. A filter as defined in claim 3, wherein said end cap supports and seals said hydrophilic filter element by means of complementary flange and recess structure.

5. A filter as defined in claim 4, said device further including a sleeve applied over said hydrophobic membrane for the purpose of preventing damage thereto and providing for a hermetic seal to said tubular body.

6. A filter as defined in claim 5, wherein said hydrophilic filter element is shaped like a cone with a tapered smaller end so that a large void space will be present between the input end of said device and the smaller end of the cone filter.

7. A filter as defined in claim 6, wherein said end cap and conical filter are attached to said body by ultrasonic welding.

8. A filter as defined in claim 7, wherein said hydrophobic membrane is held in place by spot welding.

* * * * *